United States Patent [19]
Chabin et al.

[11] Patent Number: 5,891,621
[45] Date of Patent: Apr. 6, 1999

[54] METABOLIC PATHWAY ASSAY

[75] Inventors: Renee M. Chabin, Neptune; David W. Kuo, Princeton; John F. O'Connell, Cranbury; David L. Pompliano, Lawrenceville; Kenny K. Wong, Edison, all of N.J.

[73] Assignee: Merck & Co., Inc., Rahway, N.J.

[21] Appl. No.: 936,646

[22] Filed: Sep. 24, 1997

Related U.S. Application Data

[60] Provisional application No. 60/027,331 Sep. 30, 1996 and 60/043,249, Apr. 16, 1997.

[51] Int. Cl.$^6$ .............................. C12Q 1/00; C12Q 1/37; C12Q 1/18; C12Q 1/48
[52] U.S. Cl. .................... 435/4; 435/23; 435/24; 435/32; 435/15; 435/21; 435/7.91; 435/18; 435/16
[58] Field of Search .................... 435/4, 16, 23, 435/24, 32, 15, 21, 7.91, 18

[56] References Cited

PUBLICATIONS

Athel Cornish–Bowden "Metabolic Control Analsys in Theory and Practice," Adv. Mol. Cell. Biol., vol. 11, pp. 21–64 (1995).

Tanner, et al., "Phosphinate Inhibitors of the d–Glutamic Acid–Adding Enzyme of Peptidoglycan Biosynthesis," J. Org. Chem., vol. 61, pp. 1756–1760 (1996).

Falk, et al., "Biochemical Evidence for the Formation of a Covalent Linkage between UDP–Acetylmuramate and ATP in the *Escherichia coli* UDP–N–Acetylmuramate:L–Alanine Ligase–Catalyzed Reaction," Biochemistry, vol. 35, pp. 1417–1422 (1996).

Jin, et al., "Structural Studies of *Escherichia coli* UDP–N–Acetylmuramate:L–Alanine Ligase," Biochemistry, vol. 35, pp. 1423–1431 (1996).

Auger, et al., "Synthesis of N–Acetylmuranic Acid Derivatives as Potential Inhibitors of the D–Glutamic Acid–Adding Enzyme," J. prakt. Chem., vol. 337, pp. 351–357 (1995).

Pratviel–Sosa, et al., "Over–production, purification and properties of the uridine diphosphate N–acetylmuramoyl–L–Alanine: D–glutamate ligase from *Escherichia coli*," Eur. J. Bio. Chem., vol. 202, pp. 1169–1176 (1991).

Michaud, et al., "Partial purification and specificity studies of the D–glutamate–adding and d–alanyl–D–alanine–adding enzymes from *Escherichia coli* K12," Eur. J. Biochem., vol. 166, pp. 631–637 (1987).

LeRoux et al., "Synthesis of new peptide inhibitors of the mesol–diaminopimelate–adding enzyme," Eur. J. Med. Chem., vol. 27, pp. 899–907 (1992).

Pratviel–Sosa, et al., "Effect of various analogues of D–glutamic acid on the D–glutamate–adding enzyme from *Escherichia coli*," FEMS, Microbiol. Letters, vol. 115, pp. 223–228 (1994).

(List continued on next page.)

*Primary Examiner*—Louise N. Leary
*Attorney, Agent, or Firm*—Catherine D. Fitch; Melvin Winokur

[57] ABSTRACT

An in vitro screening assay which identifies enzyme inhibitors and allows for the simultaneous assay of many enzymes. Enzyme, substrate, co-factor, etc. concentrations are optimized so that inhibitors of any one of the enzymes in the pathway are equally likely to be detected. Necessarily, the flux of substrate through each enzyme should be nearly the same during the assay, i.e., each of the enzyme catalyzed steps must be equally rate-limiting. Preferably, optimal assay conditions are predicted by computer modeling. Further, the pathway conditions are optimized through variation of enzyme, starting substrate, co-substrate and co-factor concentrations. A positive response is initially detected as a change in the amount of the product generated at the end of the enzyme cascade as compared to a standard. A sample producing a positive result can be deconvoluted.

37 Claims, 2 Drawing Sheets

PUBLICATIONS

Michaud et al., "Over–production, purification and properties of the uridine–diphosphate–N–acetylmuramoyl–L–alanyl–D–glutamate: meso–2,6–diaminopimelate ligase from *Escherichia coli*," Eur. J. Biochem. vol. 194, pp. 853–861 (1990).

Liger et al., "Over–production purification and properties of the uridine–diphosphate–N–acetylmuramate:L–alanine ligase from *Escherichia coli*," Eur. J. Biochem., vol. 230, pp. 80–87 (1995).

Gubler et al., "Overexpression, Purification, and Characterization of UDP–N–Acetylmuramyl:L–Alanine Ligase from *Escherichia coli*," Journal of Bacteriology, Feb. 1996, pp. 906–910 (1996).

Abo–Ghalia, et al., "Specificity of the uridine–diphosphate–N–acetylmuramyl–L–alanyl–D–glutamate:meso–2, 6–diaminopimelate synthetase from *Escherichia coli*," Eur. J. Biochem., vol. 53, pp. 81–87 (1985).

Bugg and Walsh, "Intracellular Steps of Bacterial Cell Wall Peptidoglycan Biosynthesis: Enzymology, Antibiotics, and Antibiotic Resistance," Natural Product Reports (1992).

Presentation by Dr. D. Pompliano, Apr. 23, 1996, to University of Minnesota Departmental Staff Meeting.

Hakes & Dixon "New Vectors for High Level Expression of Recombinant Proteins in Bacteria," Analy. Biochem., vol. 202, pp. 293–298 (1992).

Reddy, et al., Mechanistic Analysis of UDP–N–acetylmuramyl:L–alamine Ligase from *Escherichia coli* presented at Enzyme Mechamism 15th Conference, Naple, Florida, Jan. 4, 1997–Jan. 8, 1997.

METABOLIC PATHWAY ASSAY

CROSS-REFERENCE TO RELATED APPLICATIONS

The present application claims priority to provisional applications Ser. No. 60/027,331, filed Sep. 30, 1996 and Ser. No. 60043,249 filed Apr. 16, 1997.

SUMMARY OF THE INVENTION

This invention relates to an in vitro screening assay which identifies enzyme inhibitors. This invention allows for the simultaneous assay of many enzymes. The goal is to optimize the concentrations of enzymes and substrates so that inhibitors of any one of the enzymes in the pathway are equally likely to be detected. In order for this to occur, the flux of substrate through each enzyme should be nearly the same during the assay, i.e., each of the enzyme catalyzed steps must be equally rate-limiting. Consequently, optimal assay conditions can be predicted, preferably by mathematical modeling. Further, the pathway conditions are optimized through variation of enzyme, starting substrate, co-substrate and co-factor concentrations. A positive response is initially detected as a change in the amount of the product generated at the end of the enzyme cascade as compared to a standard. A sample producing a positive result can be deconvoluted. Additionally, the metabolic pathway assay of the present invention reduces the labor involved in enzyme assay: because it is pathway assay, only the initial substrate need be prepared.

One aspect of the present invention is an in vitro screening assay for a biologically active compound, which is comprised of an enzyme cascade comprising a first enzyme, a second enzyme and a substrate for the first enzyme.

Another aspect of the present invention is a method of screening for a biologically active compound which comprises combining an enzyme cascade, which is comprised of a first enzyme, a second enzyme and a substrate for the first enzyme, with a compound suspected of having biological activity, measuring the concentrations of the products of the enzymes and comparing to a standard.

Additionally, further embodiments of the present invention include, but are not necessarily limited to, any enzyme cascade assay or method of using said assay to identify biologically active compounds, wherein the cascade is comprised of any sequential combination of the enzymes which comprise the murein pathway.

BACKGROUND OF THE INVENTION

Compounds found to inhibit enzymes along metabolic pathways involving disease or pathways unique to pathogens may have useful bioactivity. Therefore, it is desirable to identify such inhibitors. Currently, assays of complete metabolic pathways in vitro are complicated by the kinetics of individual enzymes. Heretofore, component enzymes of a particular pathway were individually purified and assayed one by one. This individual assay approach also involved making the substrate for each enzyme separately. Further, attempts have been made to model behavior of metabolic pathways in vivo, in other words, by recreating the cellular environment. This approach, which has been used thus far only to study metabolic processes, has drawbacks as well. Specifically, one metabolic step is rate-limiting; therefore, when assaying using such a pathway model, it is more likely to find an inhibitor for one particular enzyme.

In particular, the present invention can be applied to the murein biosynthetic pathway. Compounds that inhibit enzymes along this pathway are expected to be antibiotics. Each gene in that pathway (murABCDEFGI, mraY, ddlA, alr) is essential for bacterial viability. The pathway is uniquely bacterial: no known eukaryotic homologues of these genes exist. There are known antibiotics (fosfomycin, cycloserine) whose molecular target is within the pathway. Additionally, this pathway is highly conserved amongst pathogenic bacteria, and thus it is expected that an inhibitor of this pathway will be a broad spectrum antibiotic.

Each of the genes in the murein biosynthetic pathway are known in the art. Table 1 lists each of the genes and their respective accession numbers in the GenBank/EMBL (European Molecular Biology Laboratory) database.

TABLE 1

| | |
|---|---|
| murA | M92358, M76452 |
| murB | L14557 |
| murC | X52644 (also in X55034) |
| murD | X51584 (also in X55034) |
| murE | X55814 (also in X55034) |
| murF | X15432 (also in X55034) |
| murG | X52644 (also in X55034) |
| murI | L14556 |
| mraY | X55034 |
| ddlA | M58467 |
| alr | M12847 |

DETAILED DESCRIPTION OF THE INVENTION

Figure 1:
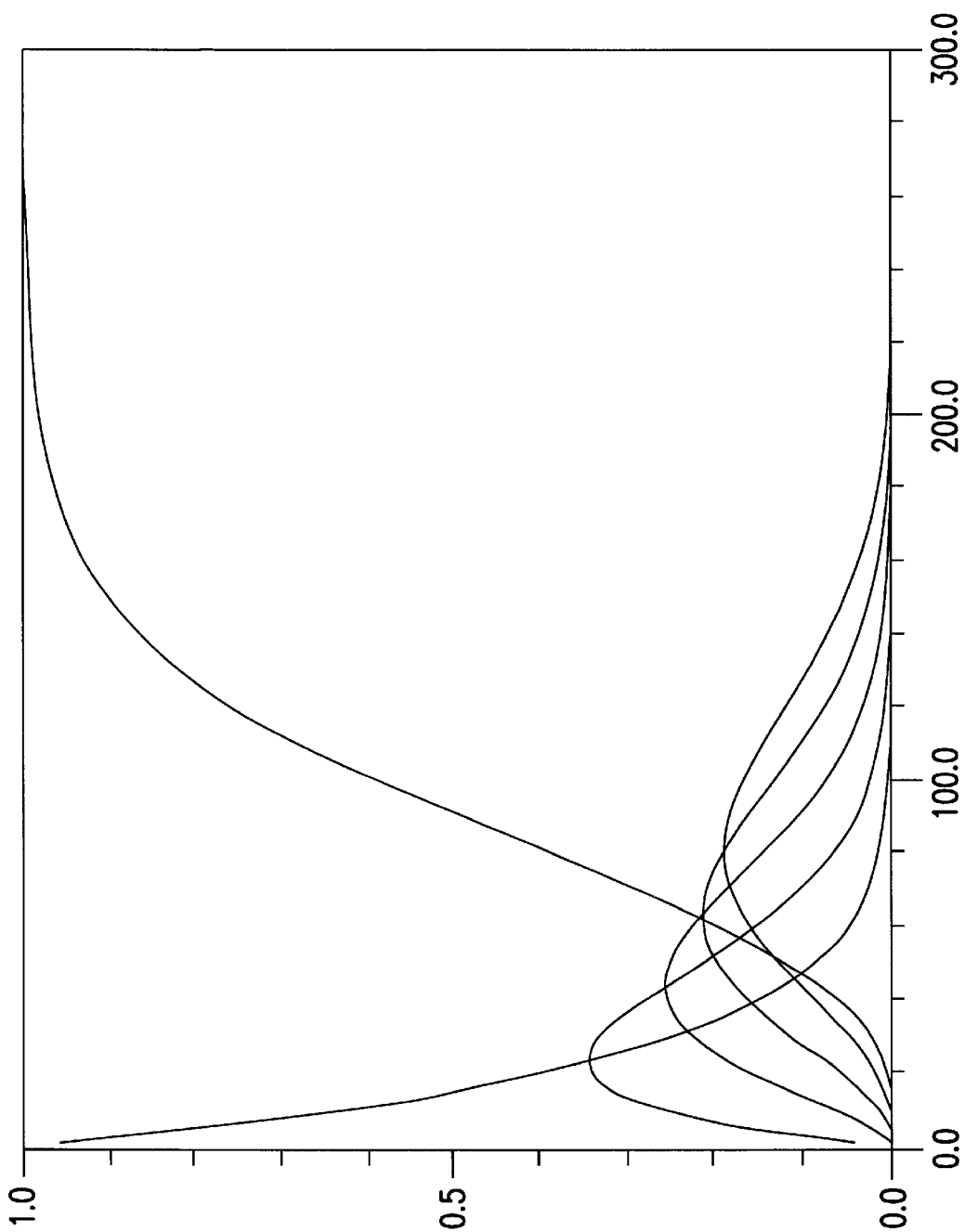
FIG. 1. A 5-enzyme/5-inhibitor enzyme system simulation is demonstrated. The concentration time course is shown for an unperturbed system. The X-axis represents time and the Y-axis represents concentration in mmol/mL. Starting from the curve highest on the Y-axis, the first curve represents the concentration of starting material, and the lower second, third, fourth and fifth curves each represent intermediate products in the enzyme cascade, and the last curve, which approaches a limit of 1.0, represents the product.

The present invention, a metabolic pathway assay, relates to an in vitro screening assay which identifies biologically active compounds, namely enzyme inhibitors. The present invention further relates to methods of identifying biologically active compounds using a pathway assay.

A metabolic pathway, or enzyme cascade, is a series of enzymes which takes a metabolite tough a series of enzyme-catalyzed reactions and transforms that metabolite into a final product or an intermediate product that will feed into another metabolic pathway.

Generally, the metabolic pathway assay of the present invention allows for the simultaneous assay of many enzymes. In the present invention, metabolic pathways are reconstructed from isolated, preferably purified, enzymes, substrate, co-substrates, co-factors, buffers, etc. Ideally, pathway conditions are optimized so as to ensure that inhibitors of any one of the enzymes in the pathway are equally likely to be detected. Preferably, this is accomplished through the use of mathematical modeling, which predicts enzyme concentrations necessary to maintain uniform flux of substrate through a particular enzyme-catalyzed step. Additionally, pathway conditions are optimized by variation of enzyme, substrate, co-substrate, co-factor, etc. concentrations. A positive response is detected as a change in the amount of product generated at the end of the enzyme cascade as compared to a standard. A sample producing a positive result may be deconvoluted.

One aspect of the present invention is an in vitro screening assay for a biologically active compound, which is comprised of an enzyme cascade comprising a first enzyme, a second enzyme and a substrate for the first enzyme.

In one embodiment of the invention, the first enzyme is suitable for changing the substrate for the first enzyme into a substrate for the second enzyme, and the second enzyme is suitable for changing the substrate for the second enzyme into a product of the second enzyme.

In one class of this embodiment, the concentration of each component in the cascade is optimized so as to maintain uniform flux of substrate through the cascade.

A second embodiment of the invention is an in vitro screening assay additionally comprising one or more co-substrates for the first and second enzymes.

In one class of this embodiment, the first enzyme is suitable for changing the substrate for the first enzyme into a substrate for the second enzyme, and the second enzyme is suitable for changing the substrate for the second enzyme into a product of the second enzyme.

In one subclass of this class, the concentration of each component in the cascade is optimized so as to maintain uniform flux of substrate through the cascade.

A third embodiment of the invention is an in vitro screening assay for a biologically active compound which is comprised of an enzyme cascade comprising a first enzyme, a second enzyme, a third enzyme, a fourth enzyme, a substrate for the first enzyme and co-substrates for the first, second, third and fourth enzymes.

In one class of this embodiment, the first enzyme is suitable for changing the substrate for the first enzyme into a substrate for the second enzyme; the second enzyme is suitable for changing the substrate for the second enzyme into a substrate for the third enzyme; the third enzyme is suitable for changing the substrate for the third enzyme into a substrate for the fourth enzyme; and the fourth enzyme is suitable for changing the substrate for the fourth enzyme into a product of the fourth enzyme.

In one subclass of this class, the concentration of each component in the cascade is optimized so as to maintain uniform flux of substrate through the cascade.

In another subclass, the first enzyme is the gene product of murC, the second enzyme is the gene product of murD, the third enzyme is the gene product of murE, and the fourth enzyme is the gene product of murF.

A species of this subclass is one in which the substrate for the first enzyme is uridyl-5'-diphosphate N-acetyl muramic acid; the co-substrates for the first enzyme are L-alanine and adenosine 5'-triphosphate; the substrate for the second enzyme is uridyl-5'-diphosphate N-acetyl muramyl-L-alanine; the co-substrates for the second enzyme are D-glutamic acid, and adenosine 5'-triphosphate; the substrate for the third enzyme is uridyl-5'-diphosphate N-acetyl muramyl-L-alanyl-γ-D-glutamic acid; the co-substrates for the third enzyme are meso-diaminopimelic acid and adenosine 5'-triphosphate; the substrate for the fourth enzyme is uridyl-5'-diphosphate N-acetyl muramyl-L-alanyl-γ-D-glutamyl-meso-dipimelic acid; and the co-substrates for the fourth enzyme are D-alanyl-D-alanine and adenosine 5'-triphosphate.

A fourth embodiment of the invention is an in vitro screening assay for a biologically active compound which is comprised of an enzyme cascade comprising a first enzyme, a second enzyme, a third enzyme, a fourth enzyme, a fifth enzyme, a sixth enzyme, a substrate for the first enzyme and co-substrates for the first, second, third, fourth, fifth and sixth enzymes.

In one class of this embodiment, the first enzyme is suitable for changing the substrate for the first enzyme into a substrate for the second enzyme; the second enzyme is suitable for changing the substrate for the second enzyme into a substrate for the third enzyme; the third enzyme is suitable for changing the substrate for the third enzyme into a substrate for the fourth enzyme; the fourth enzyme is suitable for changing the substrate for the fourth enzyme into a substrate for the fifth enzyme; the fifth enzyme is suitable for changing the substrate for the fifth enzyme into a substrate for the sixth enzyme; and the sixth enzyme is suitable for changing the substrate for the sixth enzyme into a product of the sixth enzyme.

In one subclass of this class, the concentration of each component in the cascade is optimized so as to maintain uniform flux of substrate through the cascade.

In another subclass, the first enzyme is the gene product of murA, the second enzyme is the gene product of murB, the third enzyme is the gene product of murC, the fourth enzyme is the gene product of murD, the fifth enzyme is the gene product of murE, and the sixth enzyme is the product of murF.

A species of this subclass is one in which the substrate for the first enzyme is uridyl-5'-diphosphate-N-acetyl-glucosamine; the co-substrate for the first enzyme is phosphoenolpyruvate; the substrate for the second enzyme is uridyl-5'-diphosphate-N-acetyl-enolpyruvylglucosamine; the co-substrates for the second enzyme are nicotinamide adenine dinucleotide phosphate reduced form and flavin adenine dinucleotide; the substrate for the third enzyme is uridyl-5'-diphosphate N-acetyl muramic acid; the co-substrates for the third enzyme are L-alanine and adenosine 5'-triphosphate; the substrate for the fourth enzyme is uridyl-5'-diphosphate N-acetyl muramyl-L-alanine; the co-substrates for the fourth enzyme are D-glutamic acid, and adenosine 5'-triphosphate; the substrate for the fifth enzyme is uridyl-5'-diphosphate N-acetyl muramyl-L-alanyl-γ-D-glutamic acid; the co-substrates for the fifth enzyme are meso-diaminopimelic acid and adenosine 5'-triphosphate; the substrate for the sixth enzyme is uridyl-5'-diphosphate N-acetyl muramyl-L-alanyl-γ-D-glutamyl-meso-dipimelic acid; and the co-substrates for the sixth enzyme are D-alanyl-D-alanine and adenosine 5'-triphosphate.

Another aspect of the present invention is a method of screening for a biologically active compound which comprises combining an enzyme cascade, which is comprised of a first enzyme, a second enzyme and a substrate for the first enzyme, with a compound suspected of having biological activity, measuring the concentrations of the products of the enzymes and comparing to a standard.

In one embodiment of this aspect of the invention, the concentrations of products are measured by radio-labeled HPLC.

In a second embodiment, the first enzyme is suitable for changing the substrate for the first enzyme into a substrate for the second enzyme, and the second enzyme is suitable for changing the substrate for the second enzyme into a product of the second enzyme.

In a class of this embodiment, the concentration of each component in the cascade is optimized so as to maintain uniform flux of substrate through the cascade.

A third embodiment is a method of screening for a biologically active compound which comprises combining an enzyme cascade, comprising a first enzyme, a second enzyme, a substrate for the first enzyme and co-substrates for the first and second enzymes, with a compound suspected of having biological activity and measuring the concentrations of the products of the enzymes and comparing to a standard.

In one class of this embodiment, the concentrations of products are measured by radio-labeled HPLC.

In another class of this embodiment, the first enzyme is suitable for changing the substrate for the first enzyme into a substrate for the second enzyme, and the second enzyme is suitable for changing the substrate for the second enzyme into a product of the second enzyme.

In a subclass of this class, the concentration of each component in the cascade is optimized so as to maintain uniform flux of substrate through the cascade.

A fourth embodiment of this aspect of the invention is a method of screening for a biologically active compound which comprises combining an enzyme cascade, comprising a first enzyme, a second enzyme, a third enzyme, a fourth enzyme, a substrate for the first enzyme and co-substrates for the first, second, third and fourth enzymes, with a compound suspected of having biological activity, and measuring the concentrations of the products of the enzymes and comparing to a standard.

In one class of this embodiment, the concentrations of the products are measured by HPLC.

In another class of this embodiment, the first enzyme is suitable for changing the substrate for the first enzyme into a substrate for the second enzyme; the second enzyme is suitable for changing the substrate for the second enzyme into a substrate for the third enzyme; the third enzyme is suitable for changing the substrate for the third enzyme into a substrate for the fourth enzyme; and the fourth enzyme is suitable for changing the substrate for the fourth enzyme into a product of the fourth enzyme.

In one subclass of this class, the concentration of each component in the cascade is optimized so as to maintain uniform flux of substrate through the cascade.

In another subclass, the first enzyme is the gene product of murC, the second enzyme is the gene product of murD, the third enzyme is the gene product of murE, and the fourth enzyme is the gene product of murF. Another aspect of the present invention is an antibiotic compound identified by the method of this subclass.

A species of this subclass is a method comprised of an enzyme cascade in which the substrate for the first enzyme is uridyl-5'-diphosphate N-acetyl muramic acid; the co-substrates for the first enzyme are L-alanine and adenosine 5'-triphosphate; the substrate for the second enzyme is uridyl-5'-diphosphate N-acetyl muramyl-L-alanine; the co-substrates for the second enzyme are D-glutamic acid, and adenosine 5'-triphosphate; the substrate for the third enzyme is uridyl-5'-diphosphate N-acetyl muramyl-L-alanyl-γ-D-glutamic acid; the co-substrates for the third enzyme are meso-diaminopimelic acid and adenosine 5'-triphosphate; the substrate for the fourth enzyme is uridyl-5'-diphosphate N-acetyl muramyl-L-alanyl-γ-D-glutamyl-meso-dipimelic acid; and the co-substrates for the fourth enzyme are D-alanyl-D-alanine and adenosine 5'-triphosphate.

A fifth embodiment of this aspect of the invention is a method of screening for a biologically active compound which comprises combining an enzyme cascade, comprising a first enzyme, a second enzyme, a third enzyme, a fourth enzyme, a fifth enzyme, a sixth enzyme, a substrate for the first enzyme and co-substrates for the first, second, third, fourth, fifth and sixth enzymes, with a compound suspected of having biological activity, and measuring the concentrations of the products of the enzymes and comparing to a standard.

In one class of this embodiment, the concentrations of the products are measured by HPLC.

In another class of this embodiment, the first enzyme is suitable for changing the substrate for the first enzyme into a substrate for the second enzyme; the second enzyme is suitable for changing the substrate for the second enzyme into a substrate for the third enzyme; the third enzyme is suitable for changing the substrate for the third enzyme into a substrate for the fourth enzyme; the fourth enzyme is suitable for changing the substrate for the fourth enzyme into a substrate for the fifth enzyme; the fifth enzyme is suitable for changing the substrate for the fifth enzyme into a substrate for the sixth enzyme; and the sixth enzyme is suitable for changing the substrate for the sixth enzyme into a product of the sixth enzyme.

In one subclass of this class, the concentration of each component in the cascade is optimized so as to maintain uniform flux of substrate through the cascade.

In another subclass, the first enzyme is the gene product of murA, the second enzyme is the gene product of murB, the third enzyme is the gene product of murC, the fourth enzyme is the gene product of murD, the fifth enzyme is the gene product of murE, and the sixth enzyme is the product of murF.

A species of this subclass is a method comprised of an enzyme cascade in which the substrate for the first enzyme is uridyl-5'-diphosphate-N-acetyl-glucosamine; the co-substrate for the first enzyme is phosphoenolpyruvate; the substrate for the second enzyme is uridyl-5'-diphosphate-N-acetyl-enolpyruvylglucosamine; the co-substrate for the second enzyme are nicotinamide adenine dinucleotide phosphate reduced form and flavin adenine dinucleotide; the substrate for the third enzyme is uridyl-5'-diphosphate N-acetyl muramic acid; the co-substrates for the third enzyme are L-alanine and adenosine 5'-triphosphate; the substrate for the fourth enzyme is uridyl-5'-diphosphate N-acetyl muramyl-L-alanine; the co-substrates for the fourth enzyme are D-glutamic acid, and adenosine 5'-triphosphate; the substrate for the fifth enzyme is uridyl-5'-diphosphate N-acetyl muramyl-L-alanyl-γ-D-glutamic acid; the co-substrates for the fifth enzyme are meso-diaminopimelic acid and adenosine 5'-triphosphate; the substrate for the sixth enzyme is uridyl-5'-diphosphate N-acetyl muramyl-L-alanyl-γ-D-glutamyl-meso-dipimelic acid; and the co-substrates for the sixth enzyme are D-alanyl-D-alanine and adenosine 5'-triphosphate.

Additionally, further embodiments of the present invention include, but are not necessarily limited to, any enzyme cascade assay or method of using said assay to identify biologically active compounds, wherein the cascade is comprised of any sequential combination of the enzymes which comprise the murein pathway. The enzyme pathway is mapped in Scheme 1 below.

Scheme 1

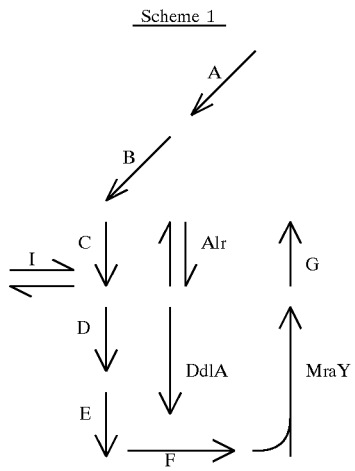

A number of substrates, co-substrates and co-factors may be necessary for the above-mentioned embodiments. Such materials include, but are not necessarily limited to: uridyl-5'-diphosphate N-acetyl-glucosamine (UDPAG); phosphoenolpyruvate; uridyl-5'-diphosphate-N-acetyl-enolpyruvylglucosamine; nicotinamide adenine dinucleotide phosphate reduced form (NADPH); flavin adenine dinucleotide (FAD); uridyl-5'-diphosphate-N-acetyl-muramic acid (UDPMurNAc); L-alanine; ATP; L-glutamic acid; UDPMurNAc-L-alanine; D-glutamic acid; UDPMurNAc-L-alanyl-γ-D-glutamic acid; meso-diaminopimelic acid; UDPMurNAc-L-alanyl-γ-D-glutamyl-meso-diaminopimelic acid; D-alanyl-D-alanine; UDPMurNAc-L-alanyl-γ-D-glutamyl-meso-diaminopimelyl-D-alanyl-D-alanine; undecaprenyl diphosphate; and undecaprenyl-diphosphoryl-MurNAc-L-alanyl-γ-D-glutamyl -meso-diaminopimelyl-D-alanyl-D-alanine.

Preferably in the present invention, the pathway is reconstructed in vitro using purified pathway components (i.e., substrate, enzymes, co-substrates, co-factors, buffers, etc.).

The enzymes which comprise a particular pathway may be obtained in a number of ways. First, enzyme-encoding gene sequences can be used to make enzymes for the assay. Each gene is cloned by PCR, or polymerase chain reaction. The genes are expressed using commercially available expression vectors or modifications thereof. Expression can be, but is not necessarily, accomplished via glutathione-S-transferase (GST), maltose binding protein (MBP), or other similar fusions. The expressed enzymes are then purified. If the enzymes were expressed by protein fusion, the enzymes are purified by affinity chromatography specific to the fusion protein used. The enzymes may then be cleaved from the protein with a suitable protease. Both free enzyme and protein-fused enzymes can be used in the assay of the present invention. Second, native enzymes may be isolated from bacterial cells. Alternatively, enzymes comprising the pathway to be assayed may be purchased if commercially available.

In one embodiment of the present invention, the known gene sequences for murC, murD, murE and murF are used to synthesize their enzyme products: UDP-N-acetylmuramoyl: L-alanine ligase; UDP-N-acetylmuramoyl- L-alanine: D-glutamate ligase; UDP-N-acetylmuramoyl-L-alanyl-D-glutamate: meso-2,6-diaminopimelate ligase; and UDP-N-acetylmuramoyl-L-alanyl-D-glutamyl-meso-2,6-diaminopimoyl-D-alanine-D-alanine synthase, respectively. The genes are cloned by PCR and expressed using a modified commercially available GST or MBP fusion expression vector, such as pGEX-KT or pMal-C. The expression vector modification with respect to MBP fusions is detailed in Reference Example 3. The GST-fusion expression vectors are referenced under Hakes, D. J. and Dixon, J. E. "New Vectors for High Level Expression of Recombinant Proteins in Bacteria" 202 *Analytical Biochemistry* 293–298 (1992). The protein expression is detailed in Reference Example 5. The expressed enzymes are purified by affinity chromatography specific to the fusion protein used in the expression or any other suitable purification method. For example, GST fusions bind to glutathione agarose columns eluted with glutathione. MBP fusions bind to amylose columns eluted with maltose. The enzyme is cleaved from the purified fusion protein by incubating with thrombin. The contaminating GST or MBP can be removed by passage of the thrombin cleavage reaction mixture through the glutathione or amylose column one more time. The free enzyme passes through without binding to the column, while the GST or MBP will specifically stick to the column. The purification of the enzyme products of murC, murD, murE and murF is detailed in Reference Examples 6–9. In one embodiment of the present invention, the free mur enzymes are used for pathway assay. In another embodiment of the present invention, GST or MBP fusions of the mur enzymes are used for pathway assay. In an embodiment of the invention, MBP fusions are utilized.

The substrate for the first enzyme likewise can be synthesized according to known processes or purchased if commercially available.

In one embodiment of the present invention wherein the enzyme cascade is comprised of the gene products of murC, murD, murE, and murF, UDPMurNAc is synthesized by a coupled MurA, MurB reaction. This synthesis is detailed in Reference Example 1.

The pathway assay also may contain a biological buffer, which maintains the requisite pH level for the specific enzyme-catalyzed reactions. Any buffer of suitable pKa range can be used.

In one embodiment of the present invention wherein the enzyme cascade is comprised of the gene products of murC, murD, murE, and murF, any suitable buffer with a pKa range of about 8 is used. In a more preferred embodiment, Bis-Tris Propane, pH 8.0 is used.

The assay also may contain a marker or tag that is useful for detection and deconvolution purposes. For instance, any suitable radioactive marker or fluorescent tag can be purchased or synthesized. Such a marker can be incorporated into the initial substrate or any other pathway component that will be metabolically incorporated into the products of the enzymes.

In one embodiment of the present invention wherein the enzyme cascade is comprised of the gene products of murC, murD, murE, and murF, $^3$H-L-alanine purchased from Amersham is used as a radioactive initial substrate.

The assay also may contain a number of co-substrates. By the term "co-substrate" is meant any agent that is metabolized and is necessary for product formation. Co-substrates can be synthesized according to known processes or purchased if commercially available.

In one embodiment of the present invention wherein the enzyme cascade is comprised of the gene products of murC, murD, murE, and murF, a number of co-substrates are used. The co-substrate for the first enzyme is L-alanine. The co-substrate for the second enzyme is D-glutamic acid. The co-substrate for the third enzyme is meso-diaminopimelic acid. The co-substrate for the fourth enzyme is D-alanyl-D-alanine. Each of these co-substrates is purchased from Sigma. Adenosine 5'-triphosphate is a co-substrate for each of the four enzymes; any suitable phosphorylating agent can be used in place of ATP.

The assay also may contain a number of co-factors. By the term "co-factor" is meant any agent that is necessary for product formation, but that is not actually incorporated into the final product. For example, $MgCl_2$ or another suitable co-factor such as $MnCl_2$ is required for cascades that comprise ATP-utilizing enzymes. Co-factors an be synthesized according to known processes or purchased if commercially available.

In one embodiment of the present invention wherein the enzyme cascade is comprised of the gene products of murC, murD, murE, and murF, $MgCl_2$ is used as a co-factor.

The assay also may contain other agents, such as stabilizing agents including, but not limited to, DTT and BSA. Such stabilizing agents protect the enzyme from loss of activity. For instance, adding DTT to a buffer will contribute to enzyme stability.

The goal is to optimize the concentrations of the enzymes and substrates so that inhibitors of any one of the enzymes in the pathway are equally likely to be detected. In order for this to occur, the flux of substrate through each enzyme should be nearly the same. In other words, each of the enzyme-catalyzed steps must be equally rate-limiting.

The necessary relative enzyme concentrations in the pathway assay can be predicted using the combination of kinetic parameters for each individual enzyme with a numeric model of the coupled sequential enzyme systems. The kinetic parameters for each individual enzyme, if unknown, can be determined through conventional enzymological methods in conjunction with a non-linear modeling of the kinetic data to extract the relevant rate constants for each enzyme. The experimentally determined kinetic parameters can then be used in a computer simulation of the sequential enzyme system. Software was devised to fit kinetic constants to experimental data and to simulate the time course of multiple enzyme systems. This approach utilizes the Runge-Kutta algorithm to solve general chemical and enzyme kinetic rate equations as non-linear, coupled differential equations. These coupled rate equations were expanded to derive partial derivatives (dyi/dkj) with respect to the rate constants. The time integrated rate equations are then used to construct a chi-squared function (goodness of fit to experimental data) and the gradient Hessian matrix which is used to directly fit the rate constants using the Levenberg-Marquardt algorithm. The approach has several advantages over the current limited methods. First, the analytic, integrated rate equation does not have to be solved. Normally, the coupled differential equations are solved (integrated) for special conditions and or special mechanisms. These special case equations are then employed to derive the chi-squared function and partial derivatives through chain-rule derivatization. This greatly limits the utility of existing methods since so few mechanisms can be handled in such a fashion.

Directly solving the coupled differential equations provides for a general method to non-linear fitting of rate constants to general mechanisms. Calculating the partial second derivative Hessian matrix allows for the calculation of the covariance and correlation matrix which is used with the calculated Student-t statistics to access the error of the derived rate constants. This approach also allows for the simulation of multiple enzyme systems under various initial conditions in which no closed form solutions either analytic or approximated are available. Thus, enzyme and chemical reaction pathways may be simulated and rate constants derived from experimental data without resorting to approximations based on initial conditions or a particular kinetic model. In particular, the time course of all components of multiple enzyme systems may be simulated under any initial concentration conditions. See Example 3.

In the case of the mur pathway, the general fitting of experimental data with general rate equations allows for the extraction of the relevant rate constants for each enzyme in the pathway. These rate constants for each individual enzyme are then used in the simulation of the sequential enzyme mur pathway. This derived data and simulations are then used to construct initial conditions for the complete sequential mur enzyme pathway assay. This is done in such a way that each sequential enzyme will produce a nearly identical product flux throughout the assay such that inhibition of any enzyme will be reflected in the measured final product concentration. Identical product flux provides a situation in which inhibition of any enzyme in the pathway is detected and that the inhibition results would be similar to assaying the enzyme individually. This type of analysis also allows for the validation of the coupled enzyme systems and a way to explore alternative mechanisms. The modeling of mechanisms and the derivations of integrated equations, time derivatives, partial rate constant (K) derivatives and their corresponding time derivations provide excellent tools to explore chemical and enzyme mechanisms.

Additionally, pathway conditions are optimized by standard optimization techniques, such as variation of enzyme, substrate, co-factor, marker, etc. concentrations.

In one embodiment of the present invention wherein the enzyme cascade is comprised of the gene products of murC, murD, murE and murF, the concentrations of the pathway components are as follows: 10 nM MurC; 20 nM MurD; 10 nM MurE; 20 nM MurF; 10 $\mu$M L-alanine; 500 nCi$^3$H-L-alanine; 100 $\mu$M D-glutamate; 100 $\mu$M meso-diaminopimelate; 100 $\mu$M D-alanine-D-alanine; 100 $\mu$M UDP-N-acetyl muramic acid; 1 mM $MgCl_2$; and 500 $\mu$M ATP. These concentrations were set by variation of enzyme, substrate, co-factor, co-substrate, and marker concentrations.

Biologically active compounds are identified via pathway assay through a series of steps. Inhibitors are initially detected by a positive response, a change in the relative amount of the product generated at the end of the enzyme cascade as compared to a standard. A sample which produces a positive response is then deconvoluted. Deconvolution can be done in a number of ways. It can be accomplished utilizing any one of a number of detection techniques, including but not limited to UV/VIS spectrometry, fluorescent spectrometry and HPLC with radio-flow detector. Preferably, it is a two step process. First, the initial data is compared to a control set of data and points to the most probable inhibition target site(s). Second, the inhibitor is reassayed against each enzyme in the pathway individually in order to verify the inhibition target site(s).

In one embodiment of the present invention wherein the enzyme cascade is comprised of the gene products of murC, murD, murE, and murF, deconvolution is accomplished through HPLC anion exchange chromatography using YMC YS-AX036 column attached to a Shimadzu HPLC system with an in-line IN/US radioflow detector. First, the HPLC profile is used to assess enzyme and substrate pool levels. Second, the inhibitor is reassayed against each enzyme in the pathway individually in order to verify the inhibition target site.

Alternatively, the pathway assay of the present invention is be adopted to a format amenable for automated, high throughput mode. In one embodiment, this format incorporates MurA, MurB, MurC, MurD, MurE and MurF using radiolabeled D-alanine-D-alanine as a tracer. This format detects only the final product of the pathway, UDP-N-acetylmuramyl-pentapeptide. The principle of separation is absorption of the reaction product onto AG1X8 resin (BioRad) followed by a washing step to remove unreacted radiolabeled D-alanine-D-alanine. Elution of the radiolabeled pathway product, UDP-N-acetylmuramyl-pentapeptide, may be accomplished using 1M salicylic acid. Inhibition of the pathway is detected as a reduction in the formation of radiolabeled UDP-N-acetylmuramyl-pentapeptide relative to a no inhibitor control. This assay can be automated in a 96 well format.

The pathway assay in this high-throughput format contains the same components as that of the HPLC-based assay, except MurA, MurB, UDP-N-acetylglucosamine (replaces UDP-N-acetylmuramyl-L-alanine), PEP, NADPH and the radiolabeled tracer, D-alanine-D-alanine (replaces radiolabeled L-alanine). In a preferred embodiment, dithiothreitol (DTT) is added to exclude out nonspecific alkylating agents.

The following non-limiting examples are presented to better illustrate the present invention.

EXAMPLE 1
The Murein Pathway

The mur pathway assay contained 100 mM Bis-Tris Propane, pH 8.0; 10 $\mu$M L-alanine (Sigma); 500 nCi $^3$H-L-ala (Amersham); 100 $\mu$M D-glutamate (Sigma); 100 $\mu$M meso-diaminopimelate (Sigma); 100 $\mu$M D-alanine-D-alanine (Sigma); 100 $\mu$M UDP N-acetyl muramic acid (enzymatically synthesized); 1 mM $MgCl_2$ ; 500 $\mu$M ATP. Equal volume of the solvent (i.e DMSO) was also added and served as a control. The final volume was 45 $\mu$l. The reaction was initiated by the addition of MurC, MurE, MurD and MurF (5 $\mu$l) at a final concentration of 10 nM, 10 nM, 20 nM, 20 nM, respectively. A 20 $\mu$l aliquot was quickly removed and mixed into 80 $\mu$l of quench buffer (300 mM $KH_2PO_4$, pH 3.5) to stop the reaction. At 30 minutes post addition of enzyme solution, a 20 $\mu$l aliquot was removed and quenched as described above. Product analysis was accomplished by HPLC anion exchange chromatography using YMC YS-AX036 column attached to a Shimadzu HPLC system. Typical sample volume was 50 $\mu$l of the quenched reaction. The mobile phase consisted of 150 mM $KH_2PO_4$, pH 3.5 at a flow rate of 1.5 ml/min. Product formation was monitored by an in-line IN/US radioflow detector.

EXAMPLE 2
The Murein Pathway assay

The mur pathway assay contained 100 mM Bis-Tris Propane, pH 8.0; 10 $\mu$M L-alanine (Sigma); 500 nCi$^3$H-L-ala (Amersham); 100 $\mu$M D-glutamate (Sigma); 100 $\mu$M meso-diaminopimelate (Sigma); 100 $\mu$M D-alanine-D-alanine (Sigma); 100 $\mu$M UDP N-acetyl muramic acid (enzymatically synthesized); 1 mM $MgCl_2$, 500 $\mu$M ATP. An inhibitor, compound 3, Tanner, et al., "Phosphinate Inhibitors of the D-Glutamic Acid-Adding Enzyme of Peptidoglycan Biosynthesis," 61 *J. Org. Chem.* 1756–1760 (1996), was added to a final concentration of 100 $\mu$M. Equal volume of the solvent (i.e DMSO) was also added and served as a control. The final volume was 45 $\mu$l. The reaction was initiated by the addition of MurC, MurE, MurD and MurF (5 $\mu$l) at a final concentration of 10 nM, 10 nM, 20 nM, 20 nM, respectively. A 20 $\mu$l aliquot was quickly removed and mixed into 80 $\mu$l of quench buffer (300 mM $KH_2PO_4$, pH 3.5) to stop the reaction. At 30 minutes post addition of enzyme solution, a 20 $\mu$l aliquot was removed and quenched as described above. Product analysis was accomplished by HPLC anion exchange chromatography using YMC YS-AX036 column attached to a Shimadzu HPLC system. Typical sample volume was 50 $\mu$l of the quenched reaction. The mobile phase consisted of 150 mM $KH_2PO_4$, pH 3.5 at a flow rate of 1.5 ml/min. Product formation was monitored by an in-line IN/US radioflow detector. Data were reported in percent inhibition based on integrated areas of the F product peak (retention time=12.5 min) of the inhibited sample relative to an uninhibited control.

EXAMPLE 3
Mathematical modeling

Figure 2:
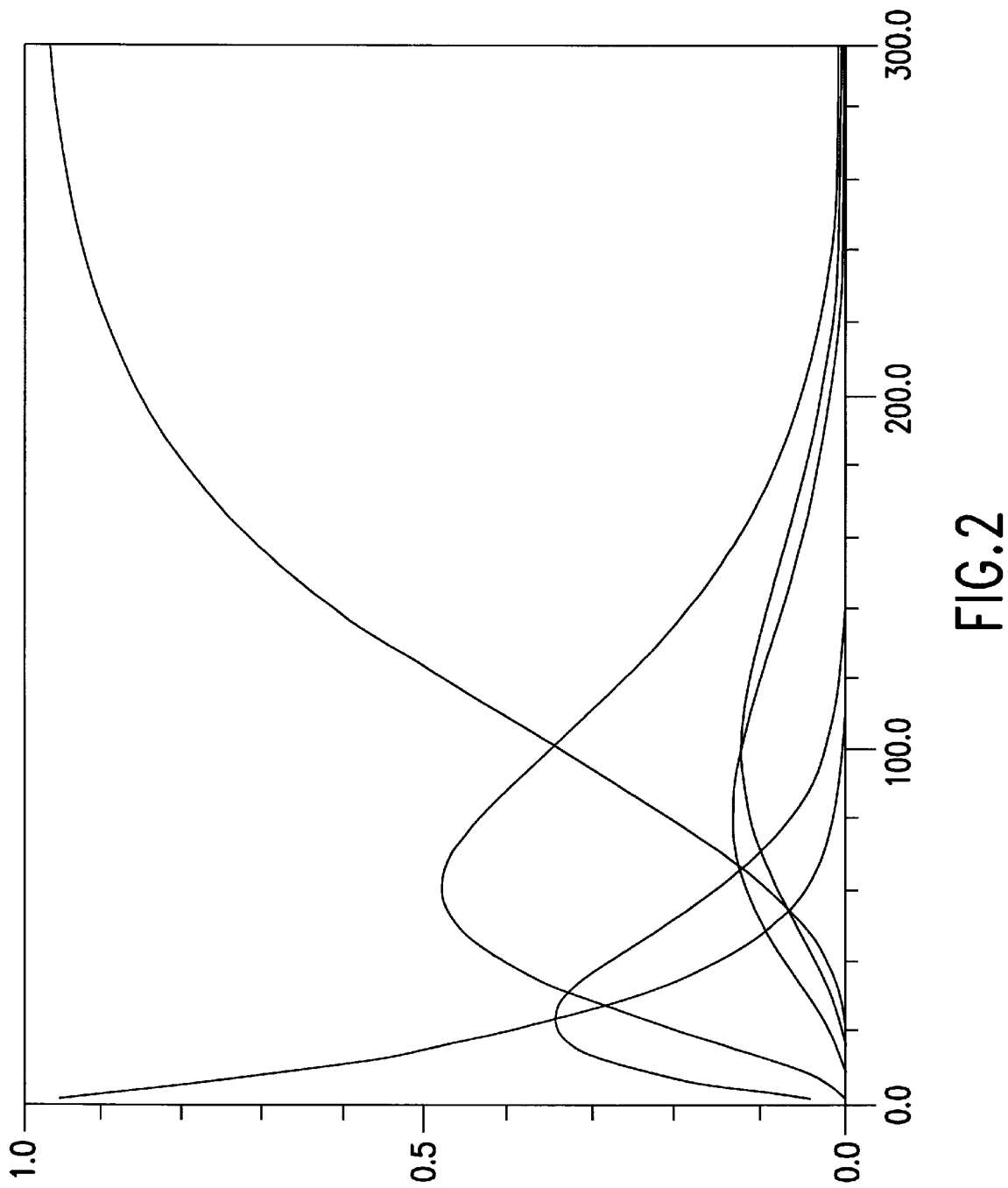
FIG. 2. A 5-enzyme/5-inhibitor enzyme system simulation is demonstrated. The concentration time course is shown for a system in which enzyme-3 is inhibited. The X-axis represents time and the Y-axis represents concentration in mmole per mL. Starting from the curve highest on the Y-axis, the first curve represents the concentration of starting material. The second, third, fourth, and fifth curves each represent the concentration intermediate products in the enzyme cascade, and the last curve, which approaches a limit of 1.0, represents the concentration of product. Compared to FIG. 2, the curve representing the concentration of intermediate product of the second enzyme reaches a much higher concentration, and the curves representing the products of the third and fourth enzyme have much lower maxima. This is due to the slower processing by the third enzyme in the cascade due to the addition of inhibitor.

A 5-enzyme/5-inhibitor enzyme system simulation is demonstrated. The concentration time course is shown for an unperturbed system (FIG. 1) and for one in which enzyme-3 is inhibited (FIG. 2). A similar analysis can be used with the mur enzyme kinetic parameters to adjust the initial enzyme concentrations such that product/substrate flux from one enzyme to the next in the sequential pathway is kept nearly identical. The example demonstrates that either enzyme inhibition or changes in enzyme concentration may be detected in the rate of final product formation.

EXAMPLE 4
The Murein Pathway

The mur pathway assay in this high-throughput format contained 100 mM Bis-Tris Propane, pH 8.0; 100 $\mu$M L-alanine (Sigma); 100 $\mu$M D-glutamate (Sigma); 100 $\mu$M meso-diaminopimelate (Sigma); 10 $\mu$M D-alanine-D-alanine (Sigma); 500 nCi$^3$H-D-alanine-D-alanine or $^{14}$C-D-alanine-D-alanine (ARC, Inc.); 12 $\mu$M UDP-N-acetyl -glucosamine (Sigma); 25 $\mu$M NADPH (Sigma); 12 $\mu$M PEP (Sigma); 500 $\mu$M DTT (Sigma); 25 mM $(NH_4)_2SO_4$ ; 5 mM KCl (Sigma); 1 mM $MgCl_2$ (Sigma); 500 $\mu$M ATP (Sigma) and 10% DMSO. The final volume was 40 $\mu$L. The reaction was initiated by the addition of MurA, MurB, MurC, MurE, MurD and MurF (typical volume was 10 $\mu$L) at a final concentration of 200 nM, 200 nM, 80 nM, 173 nM, 82 nM and 103 nM, respectively. The reaction was terminated at 60 min by the addition of 50 $\mu$L of quench buffer (500 mM $KH_2PO_4$, pH 3.5) and the volume adjusted to 250 $\mu$L by the addition of 150 $\mu$L water. Then 50 $\mu$L of AG1-X2 resin (1:1 w/v in 25 mM $KH_2PO_4$, pH 3.5) was added and incubated at room temp for 60 min. The resin was washed with 200 $\mu$L of water three times The product was eluted and collected by the addition of 50 $\mu$L of 1M salicylic acid. The eluant was then counted on a top counter after the addition of 200 $\mu$L Microscint 40 (Packard) to determine the extent of reaction.

EXAMPLE 5
The Murein Pathway

The mur pathway assay in this high-throughput format contained 100 mM Bis-Tris Propane, pH 8.0; 100 $\mu$M L-alanine (Sigma); 100 $\mu$M D-glutamate (Sigma); 100 $\mu$M meso-diaminopimelate (Sigma); 10 $\mu$M D-alanine-D-alanine (Sigma); 500 nCi$^3$H-D-alanine-D-alanine or $^{14}$C-D- alanine-D-alanine (ARC); 12 μM UDP-N-acetyl-glucosamine (Sigma); an inhibitor, fosfomycin (Sigma) was added to a final concentration of 12 μM; 25 μM NADPH (Sigma); 12 μM PEP (Sigma); 500 μM DTT (Sigma); 25 mM $(NH_4)_2SO_4$; 5 mM KCl (Sigma); 1 mM $MgCl_2$ (Sigma); 500 μM ATP (Sigma) and 10% of DMSO. The final volume was 40 μL. The reaction was initiated by the addition of MurA, MurB, MurC, MurE, MurD and MurF (typical volume was 10 μL) at a final concentration of 200 nM, 200 nM, 80 nM, 173 nM, 82 nM and 103 nM, respectively. The reaction were terminated at 60 min by the addition of 50 μL of quench buffer (500 mM $KH_2PO_4$, pH 3.5) and the volume adjusted to 250 μL by the addition of 150 μL water. Then 50 μL of AG1-X2 resin (1:1 w/v in 25 mM $KH_2PO_4$, pH 3.5) was added and incubated at room temp for 60 min. The resin was washed with 200 μL of water three times. The product was eluted and collected by the addition of 50 μL of 1M salicylic acid. The eluant was then counted on a top counter after the addition of 200 μL Microscint 40 (Packard) to determine the extent of reaction. Data were reported in percent inhibition based on the amounts of counts (cpm) eluted from the resin of the inhibited sample relative to an uninhibited control.

EXAMPLE 6

The Murein Pathway: Preincubation with inhibitor

The mur pathway assay may be arranged in preincubation mode. In this format the assay contained 100 mM Bis-Tris Propane, pH 8.0; 100 μM L-alanine (Sigma); 100 μM D-glutamate (Sigma); 100 1μM meso-diaminopimelate (Sigma); 10 μM D-alanine-D-alanine (Sigma); 500 nCi$^3$H-D-alanine-D-alanine or $^{14}$C-D-alanine-D-alanine (ARC); 12 μM UDP-N-acetyl-glucosamine (Sigma); an inhibitor, fosfomycin (Sigma) was added to a final concentration of 12 μM; 25 μM NADPH (Sigma); 500 μM DTT (Sigma); 25 mM $(NH_4)_2SO_4$; 5 mM KCl (Sigma); 1 mM $MgCl_2$(Sigma); 500 μM ATP (Sigma); MurA, MurB, MurC, MurE, MurD and MurF at a final concentration of 200 nM, 200 nM, 80 nM, 173 nM, 82 nM and 103 nM, respectively and 10% of DMSO. The final volume was 45 μL. The reaction was initiated by the addition of 5 μL of 120 μM PEP to a final concentration of 12 μM. The reaction was terminated at 60 min by the addition of 50 μL of quench buffer (500 mM $KH_2PO_4$, pH 3.5) and the volume adjusted to 250 μL by the addition of 150 μL water. Then 50 μL of AG1-X2 resin (1:1 w/v in 25 mM $KH_2PO_4$, pH 3.5) was added and incubated at room temp for 60 min. The resin was washed with 200 μL of water three times The product was eluted and collected by the addition of 50 μL of 1M salicylic acid. The eluant was then counted on a top counter after the addition of 200 μL Microscint 40 (Packard) to determine the extent of reaction. Data were reported in percent inhibition based on the amounts of counts (cpm) eluted from the resin of the inhibited sample relative to an uninhibited control.

REFERENCE EXAMPLE 1

Synthesis of UDP-N-acetylmuramic acid (UDPMurNAc)

UDPMurNAc was synthesized by a coupled MurA, MurB reaction consisting of 0.5 g (0.75 mmol) UDP-N-acetylglucosamine (Sigma), 0.38 g (0.85 mmol) phosphoenoyl-pyruvate tricyclohexylammonium salt (Sigma); 0.7 g (0.75 mmol) β-NADPH (Sigma) and 50 mM Bis-Tris-Propane pH 8.0. The reaction was run to completion at 42° C. for 3–4 hr in an inert atmosphere. UDPMurNAc was purified by a modification of the published procedure found in Jin, et al, "Structural Studies of *Escherichia coli* UDP-N-Acetylmuramate:L-Alanine Ligase," 35 *Biochemistry,* 1423–1431, (1996). The modified procedure was as follows. The reaction was ultrafiltrated using an Amicon equipped with a PM10 membrane to remove the enzymes. The reaction mixture was loaded onto a MonoQ column previously equilibrated with 10 mM triethylammonium bicarbonate buffer, pH 8.5. The column was developed with a linear gradient of triethylammonium bicarbonate from 10 to 600 mM. UDPMurNAc eluted at 150 mM concentration. Fractions were pooled and lyopholized to yielded a white solid. For the pathway assay, the solid was brought up to a concentration of typically 10 mM.

REFERENCE EXAMPLE 2

Material for Enzyme Synthesis

*E. coli* strain TOP10F' (Invitrogen) was used for plasmid construction and BL21(DE3) (Stratagene) was used for protein expression. Plasmid pMAL$^{TM}$-cl was obtained from New England Biolabs. Casamino acids, tryptone, agar and yeast extract were from Difco. D(+)-glucose, ampicillin, IPTG, 5-bromo-4-chloro-3-indolyl-β-D-galactopyranosid and benzamidine were from Sigma. Pefabloc and restriction enzymes were obtained from Boehringer Mannheim. The heavy metal substitutes for the minimal media were from Fluka. All other salts and buffer components were from Fisher. Bovine thrombin was obtained from Armour Pharmaceutical Company. Imidazole was obtained from ICH Biomedicals. Pre-cast SDS polyacrylamide gels were from Novex. Dialysis membranes were obtained from Spectrapore and Centriplus devices from Amicon. Low-Molecular Weight Protein Standards, superdex 75, Q-sepharose Fast Flow were from Pharmacia. The Talon Metal Affinity resin was obtained from Clontech. The buffer used for Talon affinity purification, buffer A, contains 10 mM Tris/HCl pH 8.0, 50 mM sodium phosphate pH 8.0, 100 mM NaCl.

REFERENCE EXAMPLE 3

Construction of pMALc-B and pMALc-H pMALc-B was constructed from pMAL™-cl by removing the Factor Xa site and part of the multiple cloning site with a Asp718-SalI restriction digest and replacing it with an annealed pair of synthetic oligonucleotides (5'-CTGGTACCGCTGGTTCCGCGTGGATCCCTCGAGTCGACTG-3' (SEQ. ID. NO.: 1); 5'-CAGTCGACTCGAGGGATCCACGCGGAACCAGCGGTACCAG-3' (SEQ. ID. NO.: 2)) which were digested with the same restriction enzyme sites and encode a thrombin site and a XhoI restriction site used for screening purposes. pMALc-H was constructed from pMALc-B after digesting with SacI and Asp718 by cloning an annealed pair of synthetic oligonucleotides (5'-TCGAGCTCCCACCATCACCATCACCACGCGAATTCGGTACCTG-3' (SEQ. ID. NO.: 3); 5'-CAGGTACCGAATTCGCGTGGTGATGGTGATGGTGGGAGCTCGA-3' (SEQ. ID. NO.: 4)) which was also digested with SacI and Asp718. This step introduced the sequence encoding six consecutive histidines and an EcoRI restriction site used for screening purposes.

REFERENCE EXAMPLE 4

Minimal Medium

Minimal medium was used throughout cloning and expression of all constructs except during the 30 minute non-selective cell recovery phase in *E. coli* transformations procedures (after the heat shock, before spreading on selective plates) when LB containing 0.5% glucose was used instead. The minimal medium is M9 medium substituted with vitamins and heavy metals as follows: 5 g/L glucose, 1 mg/L (+) biotin, 2 mg/L thiamine, 1 g/L $(NH_4)_2SO_4$, 750 mL sterile water, 4 ml heavy metal stock solution (250×), 50 mL autoclaved 10% casamino acids solution in water, 200 ml autoclaved 5×phosphate buffer and the appropriate antibiotic were used. One liter of 250×heavy metal stock solution is prepared by solubilizing 2.5 g $MoNa_2O_4.2 H_2O$, 250 mg $CoCl_2$, 250 mg $CuSO_4.5H_2O$, 2 g $MnSO_4.H_2O$, 25 g $MgSO_4.7H_2O$, 1.2 g $ZnSO_4.7H_2O$, 1.2 g $FeSO_4.7H_2O$, 5.0 g $CaCl_2.2H_2O$ and 2.5 g $H_3BO_3$ in 1N HCl, stirring the mixture overnight at room temperature and filtering it (0.2μm filter) to remove insoluble ingredients. This stock solution is stable at room temperature. For one liter of 5×phosphate buffer, dissolve 53 g K2HPO4 and 24.7 g KH2PO4 in water and autoclave. It is very important to add the phosphate buffer to the medium after the heavy metals have been dissolved together with the glucose to avoid precipitation of insoluble phosphate salts. The 10% casamino acids solution must be autoclaved and should be filtered to remove precipitate which occasionally occurs several days after preparation. Minimal medium agar plates were prepared by mixing freshly autoclaved 3% agar/water solution (approximately 90° C.) and 2×minimal medium at room temperature in a 1:1 ratio and pouring the plates immediately.

REFERENCE EXAMPLE 5

Protein expression

An overnight BL21(DE3) culture of the pMALc-H expression construct was diluted 10-fold in fresh minimal medium and grown in 2 liter baffled flasks (500 ml medium per bottle) shaking efficiently (250–350 rpm) at 37° C. to obtain a cell density of $OD_{600}$=0.8 to 1.0. The cells were collected by centrifugation (2800 g at room temperature, 10 min) and resuspended in the same amount of fresh minimal media which was pre-equilibrated to the expression temperature of choice (for MBPH/MurC, 18° C.). Cell cultures were shaken at 18° C. and, after a recovery phase of 5 minutes, induced with 0.5 mM IPTG overnight (15–20 hours). The final cell densities after expression under these conditions is usually about $OD_{600}$=12. After expression the cells were collected by centrifugation (3400 g, 4° C., 10 min) washed with ice-cold TNE (10 mM Tris/HCl pH 7.4, 100 mM NaCl, 10 mM EDTA) quick-frozen in either liquid nitrogen or on dry ice. The cell pellets can be stored for short term at −20° C. or for long term at −70° C.

REFERENCE EXAMPLE 6

Purification of MurC from pMALc-H

The full length murC gene was cloned into pMALc-H as a BglII-SalI fragment into BamHI-SalI digested pMALc-H after it was PCR amplified using the following oligonucleotides (5'-GGGCCCATCGTAAGATCTATGAATACACAACAATTGGCAAAA -3' (SEQ. ID. NO.: 5); 5'-GAGTCGACTCAGTCATGTTGTTCTTCCTCC-3' (SEQ. ID. NO.: 6)). The cell pellet from a 1 L cell culture was resuspended in 30 ml buffer A (10 mM Tris/HCl pH 8.0, 50 mM sodium phosphate pH 8.0, 100 mM NaCl) containing 1 mM benzamidine, 1 mM pefabloc and the cells were lysed by french press (20 k cell from SLM Aminco, 1500 PSI, single run at 4° C.). The cell debris was removed by ultra centrifugation (Beckman TI45, 35000 rpm, 40 min, 4° C.) and the supernatant was loaded on a metal affinity column (Talon resin, column size 2.5×7 cm) pre-equilibrated with column buffer A. The column was washed with five column volumes column buffer A and eluted with 20 mM MES (2-[morpholino]ethanesulphonic acid), 50 mM sodium phosphate pH 5.2, 100 mM NaCl. The protein containing fractions were pooled. The pH was adjusted to pH 8.2 with NaOH and the protein was treated with thrombin (7 units thrombin per mg fusion protein) for 1.5 hours at room temperature. The cleavage was terminated with 1 mM benzamidine. The reaction mixture was loaded again on the Talon resin which was pre-equilibrated with column buffer A to adjust the pH to 8.0. MurC remains in the flow-through and the column was washed with column buffer A until no more MurC eluted. The MurC containing fractions were pooled, dialyzed (MWCO 25000) for 15 hours against 10 mM Tris/HCl pH 7.4, 10 mM DTT and loaded on a Q-sepharose column (column size 2.5×5 cm) which was equilibrated with a buffer identical to the dialysis buffer. MurC was eluted from this column using a 30 minute NaCl gradient from 0 to 1 M NaCl (flow rate 2 ml/min). The MurC containing fractions which were pooled after this step usually contained 100–130 mg>95% purified (judged by Coomassie-stained SDS gel) MurC.

REFERENCE EXAMPLE 7

Purification of MurD from pMALc-H

The full length murD gene was cloned into pMALc-H as a BamHI-SalI fragment into BamHI-SalI digested pMALc-H after it was PCR amplified using the following oligonucleotides: 5'-GGGCCC- ATCGTAGGATCCATG-GCTGATTATCAGGGTAAA -3' (SEQ. ID. NO.: 7); 5'-CTGTCGACTCAACCTAACTCCTTCGCCAG-3' (SEQ. ID. NO.: 8). The cell pellet from a 1 L cell culture was resuspended, lysed and centrifuged as in the MurC purification above. The lysis SN was also loaded on metal affinity column (Talon resin, column size 2.5×7 cm) pre-equilibrated with column buffer A, washed with 5 column volumes of buffer A and eluted with the same buffer containing 100 mM imidazole. The MurD containing fractions were pooled and thrombin cleaved with 25 U/mg for 24 h at RT. The reaction was stopped with 1 mM benzamidine, 10 mM DTT were added and the protein solution dialysed against 10 mM Tris/HCl pH 7.4, 50 mM DTT (MWCO 25000) for 4 hours. The protein solution was then loaded on a Q-sepharose column (size 2.5×6 cm) pre-equilibrated with the same buffer as for the dialysis. The column was washed until no further protein eluted from the column and eluted with a 30 min NaCl gradient from 0–1M. The MurD containing fractions were pooled and concentrated (centriplus 30) to 16 mg/ml. 5 ml of this solution was further purified on a superdex75 column (column size 2.5×60 cm, buffer: 10 mM Tris pH 7.4, 150 mM NaCl, 10 mM DTT). MurD containing fractions from this column were pooled, dialysed (MWCO 25000) for 12 hours against 20 mM Tris pH 8.0, 50 mM NaCl and filtrated over a fresh Talon column (2.5×5 cm) pre-equilibrated with the dialysis buffer. MurD remains in the flowthrough. 10 mM DTT has been added to stabilize the protein after pooling. Typically 150 mg MurD>98% purified can be obtained from 1L cell culture using this procedure.

REFERENCE EXAMPLE 8

Purification of MurE from pMALc-H

The full length murE gene was cloned into pMALc-H as a BglII-SalI fragment into BamHI-SalI digested pMALc-H after it was PCR amplified using the following oligonucleotides: 5'-GGGCCCAT-CGTAAGATCTATGGCAGATCGTAATTTGCGC-3' (SEQ. ID. NO.: 9); 5'-GAGTCGACTCATGCAATCACCCCCAGCAG-3' (SEQ. ID. NO.: 10). The cell pellet from a 1 L cell culture was resuspended, lysed, centrifuged and purified on a Metal affinity column as in the MurC purification above (elution with pH 5.2 buffer). In contrast to MurC the MBPH/MurE fusion protein binds very tight to the Talon column and can be washed longer with buffer A before elution. The MurE containing fractions were pooled, the pH adjusted to pH 8.2 using NaOH and setup for thrombin cleavage with 5 U/mg thrombin for 24 hours at RT. The reaction was stopped with benzamidine (1 mM) and the solution loaded again on the Talon column which was pre-equilibrated with buffer A. MurE containing FT-fractions were pooled and dialysed (MWCO 25000) against 20 mM Tris/HCl pH 7.4, 10 mM DTT. Finally MurE was bound in this buffer to a Q-sepharose column (2.5×10 cm) and eluted with a NaCl gradient from 0–1 M NaCl in the same buffer. Typically 140 mg MurE>98% purified can be obtained from 1L cell culture using this procedure. Occasionally we further purify MurE on a size exclusion column.

REFERENCE EXAMPLE 9
Purification of MurF from pMALc-H

The full length murF gene was cloned into pMALc-H as a BamHI-SalI fragment into BamHI-SalI digested pMALc-H after it was PCR amplified using the following oligonucleotides: 5'-GTGGATCCATGATTAGCGTAACCCTTAG-3' (SEQ. ID. NO.: 11); 5'-CTGTCGACCTAACATGTCCCATTCTCCT-3' (SEQ. ID. NO.: 12). The cell pellet from a 1 L cell culture was resuspended, lysed, centrifuged and bound on a Metal affinity column as in the purifications above. Before elution the column has been washed with high salt (gradient from 0.1–1M NaCl in buffer A, 30 min, flow rate 1 ml/min) and urea (gradient from 0–1M urea in buffer A, 30 min, flow rate 1 ml/min). The column was eluted with pH 5.2 buffer (see MurC purification). The pooled fractions were adjusted to pH 8.2 and thrombin cleaved with 15 U/mg for 10 h at RT. The solution was treated with 1 mM benzamidine and re-applied to a pre-equilibrated Talon column (buffer A). FT fractions containing MurF were pooled, dialysed (MWCO 25000, buffer 20 mM Tris/HCl pH 7.4, 10 mM DTT) and further purified on a Q-sepharose column as with MurE (see above). Finally MurF was concentrated and purified by size exclusion chromatography, i.e. superdex75 (2.5×60 cm, buffer 20 mM Tris pH 8.0, 130 mM NaCl, 5 mM $MgCl_2$, 10 mM DTT). Typically >100 mg MurF>95% purified can be obtained from 1L cell culture using this procedure.

What is claimed is:

1. A kit which is comprised of an enzyme cascade comprising a first enzyme, a second enzyme and a substrate for the first enzyme.

2. The kit according to claim 1 wherein the first enzyme is suitable for changing the substrate for the first enzyme into a substrate for the second enzyme, and the second enzyme is suitable for changing the substrate for the second enzyme into a product of the second enzyme.

3. The kit according to claim 1 wherein the concentration of each component in the cascade is optimized to maintain uniform flux of substrate through the cascade.

4. The kit according to claim 1 additionally comprising one or more co-substrates for the first and second enzymes.

5. The kit according to claim 4 wherein the first enzyme is suitable for changing the substrate for the first enzyme into a substrate for the second enzyme, and the second enzyme is suitable for changing the substrate for the second enzyme into a product of the second enzyme.

6. The kit according to claim 5 wherein the concentration of each component in the cascade is optimized to maintain uniform flux of substrate through the cascade.

7. The kit according to claim 4 additionally comprising a third enzyme, a fourth enzyme, and one or more co-substrates for the third and fourth enzymes.

8. The kit according to claim 7 wherein the first enzyme is suitable for changing the substrate for the first enzyme into a substrate for the second enzyme; the second enzyme is suitable for changing the substrate for the second enzyme into a substrate for the third enzyme; the third enzyme is suitable for changing the substrate for the third enzyme into a substrate for the fourth enzyme; and the fourth enzyme is suitable for changing the substrate for the fourth enzyme into a product of the fourth enzyme.

9. The kit according to claim 8 wherein the concentration of each enzyme in the cascade is optimized to maintain uniform flux of substrate through the cascade.

10. The kit according to claim 9 wherein the first enzyme is the gene product of murC, the second enzyme is the gene product of murD, the third enzyme is the gene product of murE, and the fourth enzyme is the gene product of murF.

11. The kit according to claim 10 wherein
the substrate for the first enzyme is uridyl-5'-diphosphate N-acetyl muramic acid;
the co-substrates for the first enzyme are L-alanine and adenosine 5'-triphosphate;
the substrate for the second enzyme is uridyl-5'-diphosphate N-acetyl muramyl-L-alanine;
the co-substrates for the second enzyme are D-glutamic acid, and adenosine 5'-triphosphate;
the substrate for the third enzyme is uridyl-5'-diphosphate N-acetyl muramyl-L-alanyl-γ-D-glutamic acid;
the co-substrates for the third enzyme are meso-diaminopimelic acid and adenosine 5'-triphosphate;
the substrate for the fourth enzyme is uridyl-5'-diphosphate N-acetyl muramyl-L-alanyl-γ-D-glutamyl-meso-dipimelic acid; and
the co-substrates for the fourth enzyme are D-alanyl-D-alanine and adenosine 5'-triphosphate.

12. The kit according to claim 7 additionally comprising a fifth enzyme, a sixth enzyme, and one or more co-substrates for the fifth and sixth enzymes.

13. The kit assay according to claim 12 wherein the first enzyme is suitable for changing the substrate for the first enzyme into a substrate for the second enzyme; the second enzyme is suitable for changing the substrate for the second enzyme into a substrate for the third enzyme; the third enzyme is suitable for changing the substrate for the third enzyme into a substrate for the fourth enzyme; the fourth enzyme is suitable for changing the substrate for the fourth enzyme into a substrate for the fifth enzyme; the fifth enzyme is suitable for changing the substrate for the fifth enzyme into a substrate for the sixth enzyme; and the sixth enzyme is suitable for changing the substrate for the sixth enzyme into a product of the sixth enzyme.

14. The kit according to claim 13 wherein the concentration of each enzyme in the cascade is optimized to maintain uniform flux of substrate through the cascade.

15. The kit according to claim 14 wherein the first enzyme is the gene product of murA, the second enzyme is the gene product of murB, the third enzyme is the gene product of murC, the fourth enzyme is the gene product of murD, the fifth enzyme is the gene product of MurE, and the sixth enzyme is the product of MurF.

16. The kit according to claim 15 wherein
the substrate for the first enzyme is uridyl-5'-diphosphate-N-acetyl-glucosamine;
the co-substrate for the first enzyme is phosphoenolpyruvate;
the substrate for the second enzyme is uridyl-5'-diphosphate-N-acetyl-enolpyruvylglucosamine;

the co-substrates for the second enzyme are nicotinamide adenine dinucleotide phosphate reduced form and flavin adenine dinucleotide;

the substrate for the third enzyme is uridyl-5'-diphosphate N-acetyl muramic acid;

the co-substrates for the third enzyme are L-alanine and adenosine 5'-triphosphate;

the substrate for the fourth enzyme is uridyl-5'-diphosphate N-acetyl muramyl-L-alanine;

the co-substrates for the fourth enzyme are D-glutamic acid, and adenosine 5'-triphosphate;

the substrate for the fifth enzyme is uridyl-5'-diphosphate N-acetyl muramyl-L-alanyl-γ-D-glutamic acid;

the co-substrates for the fifth enzyme are meso-diaminopimelic acid and adenosine 5'-triphosphate;

the substrate for the sixth enzyme is uridyl-5'-diphosphate N-acetyl muramyl-L-alanyl-γ-D-glutamyl-meso-dipimelic acid; and the co-substrates for the sixth enzyme are D-alanyl-D-alanine and adenosine 5'-triphosphate.

17. A method of screening for a biologically active compound which comprises:

combining an enzyme cascade, comprising a first enzyme, a second enzyme and a substrate for the first enzyme, with a compound suspected of having biological activity; and measuring the concentration of the products of the enzymes and comparing to a standard.

18. The method according to claim 17 wherein the concentrations of products are measured by radio-labeled HPLC.

19. The method according to claim 17 wherein the first enzyme is suitable for changing the substrate for the first enzyme into a substrate for the second enzyme, and the second enzyme is suitable for changing the substrate for the second enzyme into a product of the second enzyme.

20. The method according to claim 19 wherein the concentration of each enzyme in the cascade is optimized to maintain uniform flux of substrate through the cascade.

21. The method according to claim 17 wherein the enzyme cascade additionally comprises one or more co-substrates for the first and second enzymes.

22. The method according to claim 21 wherein the concentrations of products are measured by radio-labeled HPLC.

23. The method according to claim 21 wherein the first enzyme is suitable for changing the substrate for the first enzyme into a substrate for the second enzyme, and the second enzyme is suitable for changing the substrate for the second enzyme into a product of the second enzyme.

24. The method according to claim 23 wherein the concentration of each enzyme in the cascade is optimized to maintain uniform flux of substrate through the cascade.

25. The method according to claim 21 wherein the enzyme cascade additionally comprises a third enzyme, a fourth enzyme and one or more co-substrates for the third and fourth enzymes.

26. The method according to claim 25 wherein the concentrations of products are measured by radio-labeled HPLC.

27. The method according to claim 25 wherein the first enzyme is suitable for changing the substrate for the first enzyme into a substrate for the second enzyme; the second enzyme is suitable for changing the substrate for the second enzyme into a substrate for the third enzyme; the third enzyme is suitable for changing the substrate for the third enzyme into a substrate for the fourth enzyme; and the fourth enzyme is suitable for changing the substrate for the fourth enzyme into a product of the fourth enzyme.

28. The method according to claim 27 wherein the concentration of each enzyme in the cascade is optimized to maintain uniform flux of substrate through the cascade.

29. The method according to claim 28 wherein the first enzyme is the gene product of murC, the second enzyme is the gene product of murD, the third enzyme is the gene product of murE, and the fourth enzyme is the gene product of murF.

30. The method according to claim 29 wherein the substrate for the first enzyme is uridyl-5'-diphosphate N-acetyl muramic acid;

the co-substrates for the first enzyme are L-alanine and adenosine 5'-triphosphate;

the substrate for the second enzyme is uridyl-5'-diphosphate N-acetyl muramyl-L-alanine;

the co-substrates for the second enzyme are D-glutamic acid, and adenosine 5'-triphosphate;

the substrate for the third enzyme is uridyl-5'-diphosphate N-acetyl muramyl-L-alanyl-γ-D-glutamic acid;

the co-substrates for the third enzyme are meso-diaminopimelic acid and adenosine 5'-triphosphate;

the substrate for the fourth enzyme is uridyl-5'-diphosphate N-acetyl muramyl-L-alanyl-γ-D-glutamyl-meso-dipimelic acid; and the co-substrates for the fourth enzyme are D-alanyl-D-alanine and adenosine 5'-triphosphate.

31. The method according to claim 25 wherein the enzyme cascade additionally comprises a fifth enzyme, a sixth enzyme, and one or more co-substrates for the fifth and sixth enzymes.

32. The method according to claim 31 wherein the concentrations of products are measured by radio-labeled HPLC.

33. The method according to claim 31 wherein the first enzyme is suitable for changing the substrate for the first enzyme into a substrate for the second enzyme; the second enzyme is suitable for changing the substrate for the second enzyme into a substrate for the third enzyme; the third enzyme is suitable for changing the substrate for the third enzyme into a substrate for the fourth enzyme; the fourth enzyme is suitable for changing the substrate for the fourth enzyme into a substrate for the fifth enzyme; the fifth enzyme is suitable for changing the substrate for the fifth enzyme into a substrate for the sixth enzyme; and the sixth enzyme is suitable for changing the substrate for the sixth enzyme into a product of the sixth enzyme.

34. The method according to claim 33 wherein the concentration of each enzyme in the cascade is optimized to maintain uniform flux of substrate through the cascade.

35. The method according to claim 34 wherein the first enzyme is the gene product of murA, the second enzyme is the gene product of murB, the third enzyme is the gene product of murC, the fourth enzyme is the gene product of murD, the fifth enzyme is the gene product of murE, and the sixth enzyme is the product of murF.

36. The method according to claim 35 wherein the substrate for the first enzyme is uridyl-5'-diphosphate-N-acetyl-glucosamine;

the co-substrate for the first enzyme is phosphoenolpyruvate;

the substrate for the second enzyme is uridyl-5'-diphosphate-N-acetyl-enolpyruvylglucosamine;

the co-substrates for the second enzyme are nicotinamide adenine dinucleotide phosphate reduced form and flavin adenine dinucleotide;

the substrate for the third enzyme is uridyl-5'-diphosphate N-acetyl muramic acid;

the co-substrates for the third enzyme are L-alanine and adenosine 5'-triphosphate;

the substrate for the fourth enzyme is uridyl-5'-diphosphate N-acetyl muramyl-L-alanine;

the co-substrates for the fourth enzyme are D-glutamic acid, and adenosine 5'-triphosphate;

the substrate for the fifth enzyme is uridyl-5'-diphosphate N-acetyl muramyl-L-alanyl-γ-D-glutamic acid;

the co-substrates for the fifth enzyme are meso-diaminopimelic acid and adenosine 5'-triphosphate;

the substrate for the sixth enzyme is uridyl-5'-diphosphate N-acetyl muramyl-L-alanyl-γ-D-glutamyl-meso-dipimelic acid; and the co-substrates for the sixth enzyme are D-alanyl-D-alanine and adenosine 5'-triphosphate.

37. A high-throughput in vitro screening method for detecting a biologically active compound which is comprised of:

(a) combining an enzyme cascade comprising a first enzyme, a second enzyme, a third enzyme, a fourth enzyme, a fifth enzyme and a sixth enzyme, and a labeled substrate for the first enzyme with a compound suspected of having biological activity; wherein:

the first enzyme is the gene product of murA, the second enzyme is the gene product of murB, the third enzyme is the gene product of murC, the fourth enzyme is the gene product of murD, the fifth enzyme is the gene product of murE, and the sixth enzyme is the product of murF; and (b) measuring the concentrations of the products of the enzymes and comparing to a standard, by absorbing the product of the sixth enzyme onto resin and detecting the amount of label and comparing the amount of label to control.

* * * * *